United States Patent [19]
Verdine

[11] Patent Number: 5,783,384
[45] Date of Patent: Jul. 21, 1998

[54] SELECTION OF BINDING-MOLECULES

[75] Inventor: Gregory L. Verdine, Somerville, Mass.

[73] Assignee: President and Fellows of Harvard College, Cambridge, Mass.

[21] Appl. No.: 220,272

[22] Filed: Mar. 30, 1994

Related U.S. Application Data

[63] Continuation-in-part of Ser. No. 29,331, Feb. 10, 1993, abandoned, which is a continuation-in-part of Ser. No. 819,855, Jan. 13, 1992, abandoned.

[30] Foreign Application Priority Data

Jan. 13, 1993 [WO] WIPO .................. PCT/US93/00321

[51] Int. Cl.[6] ........................................... C12Q 1/68
[52] U.S. Cl. .................................................. 435/6
[58] Field of Search ...................................... 435/6

[56] References Cited

U.S. PATENT DOCUMENTS 4,182,654  1/1980  Royer ..................................... 435/272

FOREIGN PATENT DOCUMENTS

WO 89/10931  11/1989  WIPO .
WO 91/05058   4/1991  WIPO .
WO 91/06356   5/1991  WIPO .
WO 91/19813  12/1991  WIPO .

OTHER PUBLICATIONS

Tate et al. Location of DNA–binding segment of a positive regulator, OmpR, involved in activation of the ompF and ompC genes of *Escherichia coli* FEBS Lett. vol. 242 27–30 1988.

Blanks, R. and McLaughlin, L.W., "An Oligodeoxynucleotide Affintiy Column for the Isolation of Sequence Specific DNA Binding Proteins," *Nuc. Acids Res.*, 16:10283–10299 (1988).

Bodwell, J.E., et al., "Evidence for Distinct Sulfhydryl Groups Associated with Steroid– and DNA–Binding Domains of Rat Thymus Glucocorticoid Receptors," *Biochem*, 23:4237–4242 (1984).

Boffa, C., et al., "Factors Affecting Nucleosome Structure in Transcriptionally Active Chromatin . . . RNA Synthesis," *Eur. J. Biochem.*, 194(3):811–823 (1990).

Clackson, T., et al., "Making Antibody Fragments Using Phage Display Libraries," *Nature*, 352:624–628 (1991).

Connolly, B.A., "Chemical Synthesis of Oligonucleotides Containing a Free Sulphydryl Group and Subsequent Attachment of Thiol Specific Probes," *Nucleic Acids Res.*, 13(12):4485–4503 (1985).

Corey, D.R., et al., "Generation of a Catalytic Sequence–Specific Hybrid DNase," *Biochemistry*, 28:8277–8286 (1989).

Cwirla, S.E., et al., "Peptides on Phage: A Vast Library of Peptides for Identifying Ligands," *Proc. Natl. Acad. Sci. USA*, 87:6378–6382 (1990).

Devlin, J.J., et al., "Random Peptide Libraries: A Source of Specific Protein Binding Molecules," *Science*, 249:404–406 (1990).

Ellington, A.D., et al., "In Vitro Selection of RNA Molecules That Bind Specific Ligands," *Nature*, 346:818–822 (1990).

Ferentz, A.E. and Verdine, G.L., "Disulfide Cross–Linked Oligonucleotides," *J. Am. Chem. Soc.*, 113:4000–4002 (1991).

Kang, A.S., et al., "Linkage of Recognition and Replication Functions by Assembling Combinatorial Antibody Fab Libraries Along Phage Surfaces," *Proc. Natl. Acad. Sci. USA*, 88:4363–4366 (1991).

Kison, R., et al., "Characterization of a Cysteine–Containing Peptide After Affinity Labelling of a $Ca^{2+}$–ATPase of Sarcoplasmic Reticulum With the Disulfide of 3'(2')–O–Biotinyl–Thioinosine Triphosphate," *Eur. J. Biochem.*, 787:503–511 (1989).

MacMillian, A.M. and Verdine, G.L., "Traditional Routes to FTOs: The Dedicated Monomer Strategy," *Tetrahedron*, 47:2604–2616 (1991).

MacMillian, A.M. and Verdine, G.L., "Synthesis of Functionally Tethered Oligodeoxynucleotides by the Convertible Nucleoside Approach," *J. Organic Chemistry*, 55:5931–5933 (1990).

Meloen, R.H., et al., "The Use of Peptides of Reconstruct Conformational Determinants: A Brief Review," *Ann. Biol. Clin.*, 49:231–241 (1991).

Pluckthun, A. and Ge, L., "The Rationality of Random Screening Efficient Methods of Selection of Peptides and Oligonucleotide Ligands," *Angew. Chem. Int. Ed., Engl.* 30:(3):296–298 (1991).

Tuerk, C. and Gold L., "Systematic Evolution of Ligands by Exponential Enrichment: RNA Ligands to Bacteriophage T4 DNA Polymerase," *Science*, 249:505–510 (1990).

Scott, J.K. and Smith, G.P., "Searching for Peptide Ligands with an Epitope Library," *Science*, 249:386–390 (1990).

Fidanza, J.A. and McLaughlin, L.W., "Use of a Thiol Tether for the Site–Specific Attachment of Reporter Groups to DNA," *J. Org. Chem.*, 57:2340–2346 (1992).

Lam, K.S., et al., "A New Type of Synthetic Peptide Library for Identifying Ligand–Binding Activity," *Nature*, 354:82–84 (1991).

Houghten, R.A., et al., "Generation and Use of Synthetic Peptide Combination Libraries for Basic Research and Drug Discovery," *Nature*, 354:84–86 (1991).

O'Shea, E.K., et al., "Evidence That the Leucine Zipper is a Coiled Coil," *Science*, 243:538–542 (1988).

(List continued on next page.)

*Primary Examiner*—James Ketter
*Assistant Examiner*—John S. Brusca
*Attorney, Agent, or Firm*—Hamilton, Brook, Smith and Reynolds, P.C.

[57] ABSTRACT

Methods of designing and producing sequence-specific DNA binding proteins, methods of determining the affinity of a specific binding molecule for a target and products produced by these methods are disclosed. The methods include: forming a reversible bond between a specific binding molecule and the target and determining the susceptibility of the reversible bond to reversal as a measure of the affinity of the binding molecule for the target.

14 Claims, 4 Drawing Sheets

OTHER PUBLICATIONS

Jordan, S.R. and Pabo, C.O., "Structure of the Lambda Complex at 2.5 Å Resolution: Details of the Repressor–Operator Interactions," *Science*, 242:893–899 (1988).

Pavletich, N.P. and Pabo, C.O., "Zinc Finger–DNA Recognition: Crystal Structure of a Zif268–DNA Complex at 2.1 Å," *Science*, 252:809–817 (1991).

Talanian, R.V., et al., "Sequence–Specific DNA Binding by a Short Peptide Dimer," *Science*, 249:769–770 (1990).

Zuckermann, R., et al., "Efficient Methods for Attachment of Thiol Specific Probes to the 3'–ends of Synthetic Oligodeoxyribonucleotides," *Nucleic Acids Research*, 15(13):5305–5321 (1987).

Letsinger, R.L. and Schott, M.E., "Selectivity in Binding a Phenanthridinium–Dinucleotide Derivative to Homopolynucleotides," *J. Am. Chem. Soc.*, 103:7394–7396 (1981).

Fidanza, J.A. and McLaughlin, L.W., "Introduction of Reporter Groups at Specific Sites in DNA Containing Phosphorothioate Diesters," *J. Am. Chem. Soc.*, 111:9117–9119 (1989).

Talanian, R.V., et al., "Minimum Length of a Sequence–Specific DNA Binding Peptide," *Biochemistry*, 31:6871–6875 (1992).

MacMillan, A.M. and Verdine, G.L., "Synthesis of Functionally Tethered Oligodeoxynucleotides by the Convertible Nucleoside Approach," *J. Org. Chem.*, 55:5931–5933 (1990).

5,783,384

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
      ( A ) LENGTH: 39 base pairs
      ( B ) TYPE: nucleic acid
      ( C ) STRANDEDNESS: double
      ( D ) TOPOLOGY: linear ( x i ) SEQUENCE DESCRIPTION: SEQ ID NO:1:

AAGGTAAAC GTGCAAGTCA TCGGTATAGG TCGAGAAGT       39

( 2 ) INFORMATION FOR SEQ ID NO:2:

( i ) SEQUENCE CHARACTERISTICS:
      ( A ) LENGTH: 39 base pairs
      ( B ) TYPE: nucleic acid
      ( C ) STRANDEDNESS: double
      ( D ) TOPOLOGY: linear ( x i ) SEQUENCE DESCRIPTION: SEQ ID NO:2:

AAGGTAAAC GTGCAAGTAA TCGGTATAGG TCGAGAAGT       39

( 2 ) INFORMATION FOR SEQ ID NO:3:

( i ) SEQUENCE CHARACTERISTICS:
      ( A ) LENGTH: 39 base pairs
      ( B ) TYPE: nucleic acid
      ( C ) STRANDEDNESS: double
      ( D ) TOPOLOGY: linear ( x i ) SEQUENCE DESCRIPTION: SEQ ID NO:3:

AAGGTAAAC GTGCAAGGCA TCGGTATAGG TCGAGAAGT       39

( 2 ) INFORMATION FOR SEQ ID NO:4:

( i ) SEQUENCE CHARACTERISTICS:
      ( A ) LENGTH: 24 amino acids
      ( B ) TYPE: amino acid (D) TOPOLOGY: linear (i i) MOLECULE TYPE: peptide (x i) SEQUENCE DESCRIPTION: SEQ ID NO:4:

```
Asp Pro Ala Ala Leu Lys Arg Ala Arg Asn Thr Glu Ala Ala Arg Arg
1               5                   10                  15
Ser Arg Ala Arg Lys Gly Gly Cys
                20
```

(2) INFORMATION FOR SEQ ID NO:5:

(i) SEQUENCE CHARACTERISTICS:
        (A) LENGTH: 24 amino acids
        (B) TYPE: amino acid
        (D) TOPOLOGY: linear (i i) MOLECULE TYPE: peptide (x i) SEQUENCE DESCRIPTION: SEQ ID NO:5:

```
Asp Pro Ala Ala Leu Lys Arg Ala Arg Asn Thr Glu Ala Leu Arg Arg
1               5                   10                  15
Ser Arg Ala Arg Lys Gly Gly Cys
                20
```

(2) INFORMATION FOR SEQ ID NO:6:

(i) SEQUENCE CHARACTERISTICS:
        (A) LENGTH: 24 amino acids
        (B) TYPE: amino acid
        (D) TOPOLOGY: linear (i i) MOLECULE TYPE: peptide (x i) SEQUENCE DESCRIPTION: SEQ ID NO:6:

```
Asp Pro Ala Ala Leu Lys Arg Ala Arg Asn Thr Glu Ala Ala Pro Arg
1               5                   10                  15
Ser Arg Ala Arg Lys Gly Gly Cys
                20
```

1

SELECTION OF BINDING-MOLECULES

RELATED APPLICATIONS

This Application is a Continuation-in-Part of U.S. Ser. No. 08/029,331, filed Feb. 10, 1993, now abandoned which is a Continuation-in-Part of U.S. Ser. No. 07/819,855, filed Jan. 13, 1992, now abandoned which also claims priority to PCT/US93/00321, filed Jan. 13, 1993, the teachings of which are incorporated herein by reference.

BACKGROUND OF THE INVENTION

Small molecules which bind to other molecules with specific affinity are important in many biological processes. The importance of sequence specific DNA-binding proteins in biology became apparent in the 1960's with the establishment of models for gene regulation. Because of their important roles, it would be useful to be able to design small molecules which can mimic or replace naturally-occurring molecules. However, despite considerable interest in the design and production of small binding molecules, a rational process for the design, synthesis and selection of such molecules has not yet been developed.

SUMMARY OF THE INVENTION

The present invention relates to methods of designing and producing a member of a binding pair which specifically binds to its partner. It further relates to the products resulting from the methods. Such members are referred to herein as specific binding molecules. It particularly relates to designing and synthesizing molecules which specifically bind a desired target, such as a DNA sequence; these molecules are referred to as sequence DNA binding molecules and are also the subject matter of the present invention. Molecules, such as the sequence-specific binding molecules (also referred to herein as specific binding molecules) designed by the present method can be a peptide (D-, L- or a mixture of D- and L-), a peptidomimetic, a complex carbohydrate or other oligomer of individual units or monomers which binds specifically to its binding partner (e.g., to DNA). The present invention further relates to molecules, particularly sequence-specific DNA molecules, designed and produced by the present method and to uses therefor. Specific binding molecules produced by the present method can be used in any application in which predictable or specific joining of two members of a binding pair is desired.

In one embodiment, sequence-specific DNA binding molecules produced by the methods described herein, are useful as gene regulatory molecules, such as molecules which mimic the tight and specific DNA binding characteristics of transcription factors, which play important roles in regulation of in vitro and in vivo of gene transcription by increasing or decreasing the rate of mRNA synthesis. Most commonly, genes are regulated at the level of transcription by proteins, referred to as transcription factors, which bind promoter DNA. A critical step in gene regulation by transcription factors is binding a factor to its specific, or target, DNA sequences in the promoter. Sequence-specific DNA binding molecules designed and produced by the present method can be used as molecules which mimic the tight and specific DNA binding characteristics of transcription factors and, as a result, exert control over gene expression. Sequence specific DNA binding molecules can be used, for example, to control (enhance or repress) gene expression in vitro and in vivo and, thus, serve as the basis for development of new therapeutic strategies for treating diseases or conditions in which there is a genetic defect. For example,

2 a sequence-specific DNA binding molecule of the present invention can be used as an artificial or synthetic transcription repressor which is designed to bind a particular promoter and inhibit transcription of the gene under its control. An artificial or synthetic transcription repressor can be used to inhibit expression of a gene whose over-expression is associated with a disease or condition. Genetic diseases showing dominant inheritance, such as Huntington's disease, are promising candidates for counteraction by transcriptional inhibitors designed and produced by the method of the present invention.

The present method of designing and producing a sequence-specific binding molecule is exemplified herein by the method of designing and producing a sequence-specific DNA binding molecule, particularly, a sequence-specific DNA binding peptide. In the present method of designing and producing a sequence-specific DNA binding peptide, the following steps are carried out:

A desired or target molecule (e.g., a desired or target DNA sequence, or molecule) is synthesized or otherwise provided, which contains a first moiety capable of forming a reversible bond with a second moiety. The target DNA sequence is one for which a sequence specific binding molecule, particularly a sequence specific DNA binding peptide, is to be designed and produced. The target DNA sequence is combined with a test-binding molecule, which contains a moiety capable of forming a reversible bond with the moiety present on the target sequence, such as the target DNA sequence. The test-binding molecule (also referred to herein as test-molecule) comprises a unit such as an amino acid residue, to be assessed for its ability to bind to the desired DNA sequence. The resulting combination of target DNA sequences and test-molecules is maintained under conditions that are appropriate for the formation of a reversible bond between the first moiety (i.e., on the DNA sequence) and the second moiety (i.e., on the test-molecule) and binding of the unit being assessed to a region of the target sequence. Thus, under the appropriate conditions, DNA sequence-test-binding molecule complexes are formed, or produced. (see FIG. 1).

These complexes are then subjected to conditions under which the reversible bond between the moiety on the DNA sequence and the moiety on the test-molecule is reversed (i.e., disrupted or broken). Under a set of specified conditions, if the unit of the test-molecule is bound tightly to the DNA sequence (i.e., in a site-specific manner) the test-molecule will remain bound to, or associated with, the desired DNA sequence. However, if the unit of the test-molecule is weakly bound to the DNA sequence, under the same specified conditions, the test-molecule will easily dissociate from the desired DNA sequence. Thus, a mixture is produced which contains complexes of the test-molecule bound to the desired target sequence, uncomplexed target molecules and uncomplexed test-molecules. In the case in which a sequence-specific DNA-binding molecule (e.g., a DNA binding peptide) is being produced, the resulting mixture contains complexes, uncomplexed target DNA sequence and uncomplexed test molecules.

The identity of the test-molecule present in the complexes, and the order of the units comprising the test-molecule, is determined by the present method by carrying out the above-described process. The process is carried out a sufficient number of times to identify a binding partner, such as a DNA binding protein, of appropriate makeup and sufficient length to bind to the target DNA and remain bound to the DNA, and subsequently determining the identity and order of the units (e.g., amino acid residues) in the binding partner produced. With each subsequent cycle, the test-molecule includes one more unit to be assessed than the test-molecule of the previous cycle; the test-molecule in the complex which is formed also has one additional unit than the complex in the previous cycle. Thus, following the method described herein, a sequence-specific DNA binding molecule is designed and produced.

In a preferred embodiment, the moiety present on the target DNA and on the target molecule is a thiol group, the reversible bond formed between the two moieties is a disulfide bond, the test-molecule is a peptide and the unit to be assessed is an amino acid residue. In this embodiment, a DNA molecule of a desired sequence which contains a thiol group attached at a specific site on the sequence is combined with a synthetic peptide which also contains a thiol group. The peptide has the formula $CO_2$H-Cys-Xaa-$NH_2$. The DNA molecule and the peptide bind, or associate, via the formation of a reversible disulfide bond, thus, forming a DNA-peptide complex.

In another embodiment, a mixture of peptides can be used, all of which have the formula $CO_2$H-Cys-Xaa-$NH_2$ and each of which differs in the amino acid residue Xaa (Xaa can be any amino acid residue which lacks an —SH group). In either embodiment, each peptide will have a different association constant for the DNA sequence, and these differences will affect the reversibility, or reducibility, of the disulfide bond.

Under reversing conditions, such as subjecting the formed complexes to a thiol gradient, the peptides are released from the DNA sequence according to their DNA association constants. The strength of the disulfide bond in a disulfide-linked peptide-DNA complex is directly related to the strength of the peptide-DNA association. This relationship permits screening of tight-binding peptides from a mixture of peptides. It is reasonable to expect that the peptide that remains complexed to the DNA sequence under conditions using the highest concentration of thiol binds tightest to the DNA.

This screening process can be repeated in subsequent cycles with a peptide which has one additional amino acid residue designated Xaa, in each cycle. The identification of each Xaa residue can be determined by conventional methods, such as peptide sequencing or UV absorption. The order of the next residue of the peptide, resulting in the tightest binding to the DNA sequence is determined.

Thus, the method described herein is a rational method for the design, selection and production of molecules that bind in a site-specific manner, to desired DNA sequences. Examples of binding molecules include oligomeric molecules in which units can be added or removed (e.g., D-, L-, or DL-peptides, peptidomimetic compounds or complex carbohydrates).

Molecules made by the methods of the invention can be used to regulate a wide variety of in vitro and in vivo biological processes which depend on the site specific interaction of one molecule with another molecule. These processes include, for example, processes mediated by the binding of a peptide with a nucleic acid, or of a peptide with a peptide. Binding molecules which bind with a nucleic acid can be used to prevent gene activation by blocking the access of an activating factor to its sequence element, repress transcription by stabilizing duplex DNA or interfering with the transcriptional machinery, or carry out targeted DNA modification by delivering a reagent to a specific sequence. For example, in in vitro cell culture, it may be desirable to inhibit the transcription of a gene encoding a cellular toxin, or any other gene product whose activity one wishes to abrogate, as desired, during cell culture. Such a binding molecule can be identified using the methods described herein. Binding molecules which bind to peptides can be used to mediate or otherwise participate in, various processes such as antibody-antigen interactions, enzyme substrate interactions, hormone-receptor interactions, and lymphokine-receptor interactions.

Because the methods of the invention are chemical rather than biological, they can be used to select or discover binding molecules which are not normally synthesized by living organisms, such as peptides which include D-amino acids or nonbiogenic polymers (e.g., polymers derived from polyethylene glycol or nonnatural carbohydrates). Thus, this method is especially useful to identify and evaluate new substances, or drugs, with specific binding activity. For example, substance with DNA binding specficity can be identified which binds to promoter DNA, thus acting as a transcriptional blocker. This newly-identified transcription blocking substance can be used in both in vitro and in vivo transcription process.

Methods of the invention described herein can be used to optimize a single or small number of modifications, such as a single or small number of positions in a polymer, at each cyclic step and thus avoid steps in which extremely large numbers of species are screened.

Other advantages and features will become apparent from the following descriptions and from the claims.

DETAILED DESCRIPTION OF THE INVENTION

Figure 1:
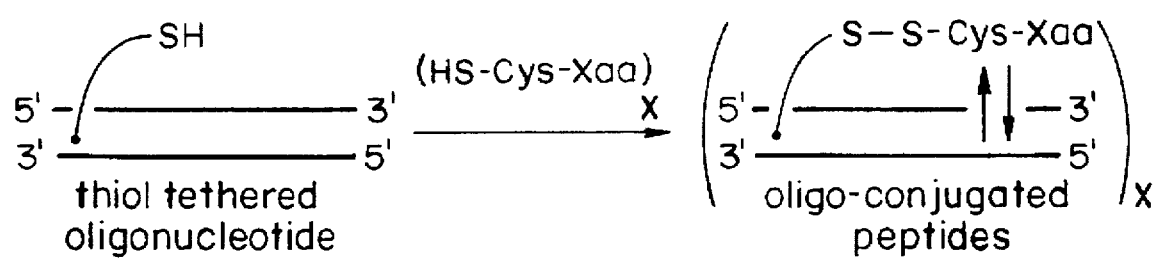
FIG. 1 is a schematic representation of the reaction between a thiol-tethered oligonucleotide and a mixture of —SH-containing peptides.

The present invention relates to methods of designing and producing a member of a binding pair which specifically binds to its partner as well as to the products resulting from these methods. Such members are referred to herein as specific binding molecules. It particularly relates to methods of designing and synthesizing molecules which specifically bind a desired DNA sequence (i.e., sequence-specific or site-specific DNA binding molecules).

Specific binding molecule (also referred to herein as binding molecule), as used herein, refers to an entity, e.g., a molecule, or a portion of a molecule, which binds to a target. Preferably, a specific binding molecule is susceptible to a plurality of successive or serial modifications, e.g., in the case of a polymeric molecule, the addition of monomeric units to the polymeric chain. Preferably, the binding affinity of a specific binding molecule with the target can be evaluated before and/or after successive modification of the specific binding molecule. A specific binding molecule is capable of reversible attachment to a target, preferably via a tether.

Test-binding molecule (or test-molecule), as used herein, refers to a specific binding molecule, some or all of the structure of which is evaluated for inclusion in the final structure of a specific binding molecule. For example, in determining the structure of a peptide, the intermediate or candidate peptides screened for binding affinity are referred to as test-binding peptides. The specific binding molecule, e.g., a final full length peptide, which is the product of the entire process, can be referred to as a final or finished specific binding molecule.

Target, as used herein, refers to an entity with which a specific binding molecule binds. Methods of the invention optimize binding affinity between a target and a specific binding molecule. A target can be a molecule, a portion of a molecule, or an aggregate of molecules. A target and a specific binding molecule can be separate molecules, or they may be different moieties on one molecule. A target includes a target site. A target is capable of reversible attachment to a binding molecule via a tether. Examples of targets include: nucleic acids (e.g., RNA or DNA, double stranded DNA, single stranded DNA, or supercoiled DNA), peptides or proteins (e.g., enzymes, receptors or antibodies), carbohydrates, and other molecular structures, such as nucleic acid-protein complexes, chromatin or ribosomes, lipid-bilayer containing structures, such as membranes, or structures derived from membranes, such as vesicles.

Target site or specific site, as used herein, refers to a site on a target to which a specific binding molecule binds. Methods of the invention optimize binding affinity between a specific binding molecule and a target site on a target. In the case of polymeric target molecules, a target site will usually include a specific sequence of monomeric subunits or a three dimensional structure. The actual structure (e.g., the chemical structure, or three dimensional structure) of the target site need only be known with enough particularity to allow formation of a reversible bond to the target. Preferably, the molecular interactions between a binding molecule and a target site are noncovalent and have energies of less than 25 kcal/mol at 25° C. These molecular interactions include hydrogen bonds, Van de waals interactions and electrostatic interactions.

Aggregate of molecules, as used herein, refers to two or more molecules which are connected by covalent or non-covalent interactions.

Tether, as used herein, refers to a structure which includes a moiety capable of forming a reversible bond with another moiety (e.g., a moiety on another tether) and (optionally) a spacer element. Alkane chains are suitable spacer moieties.

Reversible bond, as used herein, refers to a bond linking a binding molecule and a target (i.e., a binding pair) which is thermodynamically stable but capable of being broken by a reversing agent which is a physical or chemical agent capable of breaking the bond. For any given bond an appropriate reversing agent can be readily chosen based on the chemical nature of the bond. For example, a reversing agent for a disulfide bond is a reducing agent such as thiol. The reversible bond is between a tether on a specific binding molecule and a tether on a target, a bond between tether on a specific binding molecule and a target, a bond between a specific binding molecule and a tether on a target, or a bond directly between a target and a specific binding molecule. By thermodynamically stable is meant a bond whose strength is greater than 10, preferably greater than 20, more preferably greater than 50, even more preferable greater than 65, but preferably less than 100 Kcal/mol at 25° C.

Suitable examples of reversible bonds include: $R_1$-S-S-$R_2$, $R_1$-S-Cd-S-$R_2$, and $R_1$-S-Hg-S-$R_2$ wherein $R_1$ includes a binding molecule or entity and $R_2$ includes a target and the reversible bond is within the underlined area. Also included are bonds in which a metal (e.g., $Fe^{3+}$, $Co^{2+}$, $Ni^{2+}$, $Cu^{2+}$, $Zn^{2+}$, $Cd^{2+}$, or $Hg^{2+}$) is complexed between a multidentate ligand (i.e., a ligand having two (or more) moieties with which to complex an atom or group, preferably a metal atom) on a binding molecule, wherein a moiety on the binding molecule can be, e.g., S, N, or an imidazole group, and e.g., a multidentate ligand on a target, wherein a moiety on the target can be S, N, or an imidazole group. Examples of multidentate ligands follow:

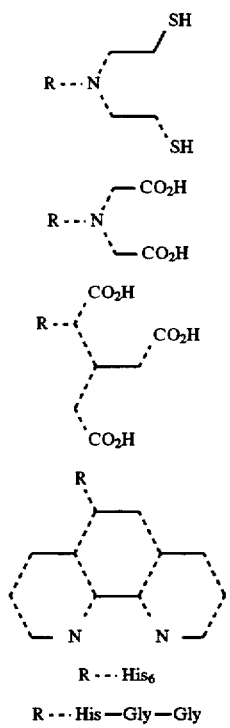

R - - - His₆

R - - - His—Gly—Gly wherein R can be either a binding molecule or a target. Any combination of multidentate ligands and monodentate ligands (i.e., a ligand having one moiety with which to complex a metal or other atom or group) can be used in the invention. For example, a binding molecule having a multidentate ligand and a target having a multidentate ligand, a binding molecule having a monodentate ligand and a target having a monodentate ligand, or a binding molecule having a monodentate ligand and a target having a multidentate ligand can be used.

Methods of the invention can be used to design specific binding molecules which bind to a target site (i.e., a specific sequence) on a target molecule. These methods include an iterative process comprising succesive cycles of: (1) modifying a test-binding molecule (also referred to as a test-molecule) ; and (2) evaluating the affinity of the modified test-binding molecule for a target site on the target molecule.

The evaluation includes evaluating the relative affinity of a test-binding molecule for a target site as compared with other test-binding molecules in a pool, or mixture of test-binding molecules. The affinity of the test-binding molecule for the target can be determined by forming a reversible bond between the test-binding molecule and the target. The susceptibility of the reversible bond to reversal is related to the affinity of the test-binding molecule for the target site on the target. In most applications a number of species of test-binding molecules, representing alternative modifications of a test-binding molecule (i.e., modifications of the initial test-binding molecule or a test-binding molecule from the previous cycle of the method) are evaluated simultaneously at each cycle. The structure of the species (at each cycle) which gives the optimum results is chosen to supply an element of the structure of the final specific binding molecule.

Thus, application of the method described herein, results in the elucidation of a preferred structure for the final binding molecule. While any molecule or combination of molecules which can be subjected to such a process can be used as a test-binding molecule, a particularly useful application of methods described herein, involve the generation of DNA binding peptides.

The synthesis and identification of a peptide which can bind to a sequence specific target site on a target DNA molecule can be performed as follows. A moiety capable of forming a reversible bond with a moiety on the test-binding molecule is attached to target DNA molecules. For example, a sulfhydryl group is tethered by an alkane chain to a site such as a site in a major or minor groove in a DNA molecule. In one embodiment, the DNA-$[C]_n$-SH is then attached to an immobilizing matrix. The DNA-$[C]_n$-SH molecules are then complexed, via a disulfide bond, to a mixture of synthetic peptides and placed in a chromatography column as shown in FIG. 1. X in FIG. 1 represents the number of species of peptides in a mixture of peptides. The curved line connecting the peptide to the DNA target represents the tether. The vertical arrows between the peptide and the DNA target represent the specific binding molecule/target site interaction, which, preferably, is the interaction the method optimizes.

The synthetic peptides are all of the formula $CO_2H$-Cys-Xaa-$NH_2$ (where Xaa equals any amino acid residue which lacks an -SH group). Either or both the N or C terminal can be modified, or blocked, as in the structure $HN_2CO_2$-Cys-Xaa-$NHCO_2CH_3$, to prevent unwanted interaction between the specific binding molecule and the target. Amino acids may be added at either end of the molecule.

The mixture of synthetic peptides includes a variety of species (i.e., a plurality of peptides of different sequences) with differences in sequences arising from various candidate residues occupying the second (Xaa) position in different peptides. The candidate residues may be any moiety which lacks an -SH group and which can be incorporated into the peptide chain, including, for example, D- or L-amino acids, naturally occurring or non-naturally occurring amino acids, or $\alpha$-, $\beta$-, or $\gamma$-amino acids.

Figure 2:
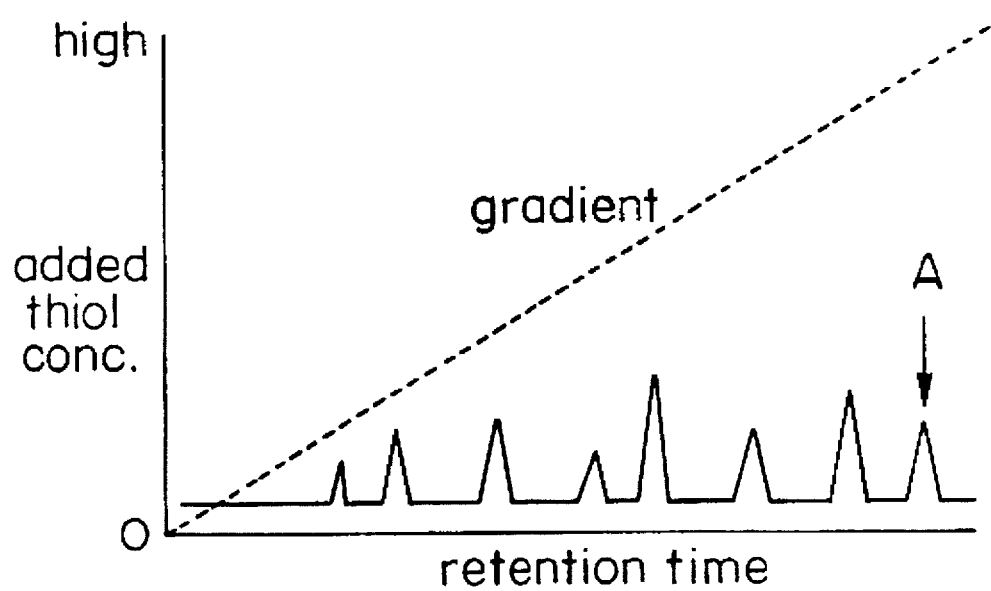
FIG. 2 is a graph of a hypothetical reduction-elution profile.

The test-binding molecule will have different binding affinities for the target DNA sequence, and these differences will affect the reducibility of the disulfide bond between the peptide and the DNA molecule with which it is complexed. In one embodiment, passage of a thiol gradient through the peptide-DNA column results in the release of the peptides according to the susceptibility of the binding molecule-target disulfide bond to reduction (i.e., reversal). This results in an elution profile which reflects the differences in susceptibility to reduction and thus the differences in the target DNA binding constants between the various dipeptides and the target. The later a dipeptide elutes, the higher its binding affinity for the target DNA sequence. Inspection of the elution profile of the dipeptides allows determination of the optimal residue at the second position. FIG. 2 shows a hypothetical elution profile. The concentration of thiol is represented by a dashed line and the elution profile by a solid line. The peak labeled A represents the species with the highest binding affinity for the target.

The entire process is repeated with a set of tripeptides. For example, $CO_2H$-Cys-XAA-Xaa-$NH_2$, where XAA is the optimum second position residue and Xaa is defined as above, is cycled through the process to determine the optimum residue for the third position in the binding peptide. Subsequent cycles extend the sequence of the binding peptide to the desired length. The desired length can be a predetermined number of amino acid residues, or can be a length at which the binding molecule exhibits useful or optimum binding affinity and/or sequence specificity.

While the peptides are lengthened by one residue per cycle in the above example, it is also possible to perform more than one modification, (e.g., to add 1, 2, 3, 4, or more residues) per cycle. When used in conjunction with conventional solid-phase-peptide synthesis technology, this strategy allows the generation of DNA binding peptides of desired lengths.

Choice of the Reversible Bond or Tether Sites

The site at which the reversible bond or tether is placed (on both specific binding molecule and target) should be chosen so as to allow a specific binding molecule coupled to the target unhindered access to the target site on the target. Stearic hindrance imposed by the location or structure of the bond or tether(s) can interfere with the correlation between bond reversibility and binding molecule-target site affinity. The inclusion of a spacer element can reduce stearic hindrance. For example, an alkane of appropriate length can be used to provide both flexibility and sufficient separation between the binding molecule and the target site.

When a nucleic acid is the target molecule a nucleic acid of any strandedness and of any topology can be used in methods of the invention. In the case of double stranded DNA, the tether can be located in a major or minor groove close to the target sequence, but not so close as to result in stearic hindrance to binding from strain on the bond between the binding peptide and the target.

The reversible bond or tether can be located such that either binding molecule-target interactions or binding molecule-solution interactions are favored. For example, in the case of an essentially linear target, such as double stranded DNA, the reversible bond or tether can be placed at or near a terminus of the molecule to favor binding molecule-solution interactions, or in the central areas (away from the termini), to favor binding molecule-target interactions.

A tether can be attached to DNA, or the reversible bond formed, on a base at any exocyclic amine or any vinyl carbon, such as the 5 or 6 position of pyrimidines, 8 or 2 positions of purines, at the ultimate 5' or 3' carbons, at the sugar phosphate backbone, or at internucleotide phosphorus atoms.

Choice of Reversible Bonds and Tethers

In methods of the invention described herein, the binding molecule is conjugated to, or associated with, the target by a reversible bond. In some embodiments the reversible bond is between a tether on the target and a tether on the specific binding molecule. In embodiments with two tethers, the tether on the binding molecule can be the same as the tether used on the target. Alternatively, different tethers can be used on each. In other embodiments only one tether is used, and in some embodiments the reversible bond is formed directly between the binding molecule and the target.

The tethers and the reversible bond should have the following characteristics. A tether (or reversible bond) should be capable of attachment to the target without substantial alteration of the three dimensional structure of the target. For example, the reversible bond or tether-bearing-target should remain similar enough in conformation to the in vivo target so that the binding molecules generated will recognize and bind to the in vivo target with a useful affinity and site specificity.

Additionally, the reversible bond formed between the target and the binding molecule should reversibly couple, by a covalent or ionic bond, the target to the binding molecule. The susceptibility to reversal, or breakage, of the reversible bond formed between the target and the binding molecule should vary with the affinity of the binding molecule for the target site on the target. The tether or tethers should be of appropriate length and flexibility such that the binding molecule has free access to the target site, and under the conditions used in methods of the invention, the reversible bond and/or tethers should be substantially unreactive with other sites on the binding molecule or target molecule.

Thiol groups are suitable moieties for forming a reversible bond. A reversible bond, e.g., a disulfide or metal-bridged disulfide bond, formed between -SH groups can be broken by contacting the bond with a reducing agent. In the case of a metal bridged disulfide, the reversible bond can be reversed with a ligand which competes with the metal atom for its position in the bridge. When the binding molecule is a peptide, the amino acid residue, cysteine, is a convenient source of an -SH group for use as the binding molecule tether. Alkane chains are suitable spacer moieties.

Methods for attaching tethers to targets, such as nucleic acid molecules, are known to those skilled in the art. (MacMillan et al., *Tetrahedron* 47:2603–2616 (1991); MacMillan et al., *J. Org. Chem.* 55:5931–5933 (1990); Ferentz et al., *J. Am. Chem. Soc.* 113:4000–4002 (1991); Zuckerman et al., *Nuc. Acid Res.* 15:5305 (1987); Connolly et al., *Nuc. Acid Res.* 13:4485 (1985); Letsinger et al., *J. Am. Chem. Soc.* 103:7394–7396 (1981); Fidanza et al., *J. Am. Chem. Soc.* 111:9117–9119 (1989)).

In one embodiment of the method described herein, where the reversible bond between the binding molecule and the target is disrupted with a reversing agent, it is convenient to immobilize the target molecule before exposure to the reversing agent. This can be done by attaching, or linking the target to a matrix, such as a resin. Methods for attaching molecules to resins are known to those skilled in the art.

Formation of Test Binding Molecule-Target Complexes

Test-binding molecules (i.e., putative or candidate binding molecules) can be synthesized by methods known to those skilled in the art. (See, for example, O'Shea, E. K., et al., *Science* 243:538–542 (1989); Talanian, R. V., et al., *Science* 249:769–771 (August 1990); Talanian, R. V., et al., *Biochem.* 31:6871–6875 (1992); (MacMillan, A. M., and Verdine, G. L., *J. Org. Chem.* 55:5931 (1990); Ferentz, A. E., and Verdine, G. L., *J. Am. Chem. Soc.* 10 113:4000–4002 (1991)).

In one embodiment, binding of peptides to thiol-tethered DNA via formation of a disulfide bond can be performed as follows. Peptides can be bound quantitatively to a thiol-tethered DNA molecule that is bound to a polymer resin, by formation of a disulfide bond between the DNA and the peptides. In these experiments, the object is to bind approximately 100% of the peptides to the resin-bound DNA, hence, an excess (2–10-fold mole excess based on the thiol-containing DNA strand) of resin-bound DNA, relative to moles of thiol groups (or disulfide groups) on the peptides is used.

The resin-bound DNA is prepared in the reduced state by treatment with common disulfide-reducing agents (alkanethiols or borohydride compounds). This incubation can be done in a batch mode or by passage of reagents through a column containing the resin-bound DNA. The excess reducing agents can be removed by filtration (batch mode) or elution (column mode).

Charging of the peptides onto the resin can either be done in batch mode or column mode. In either case, the thiol group of the peptides will first be activated by conversion to the corresponding 2-thiopyridyl or 5-thio-2-nitrobenzoyl disulfide, using standard methods.

The activated peptides, in deaerated buffer, pH 7–9 (for example 50 mM Tris, pH 8.0) will be incubated with the reduced DNA-bound resin either with shaking or stirring (batch mode) or with recirculation (column mode). Alternatively, the resin-bound DNA can be prepared as the 2-thiopyridyl or 5-thio-2-nitrobenzoyl disulfide, and the reduced peptides bound as described above.

The binding reactions can be quantified by UV measurements, monitoring release of the pyridine-2-thione or 5-thio-2-nitrobenzoate chromophores. Alternatively, the amount of peptides bound to the resin or free in solution can be quantified by a routine ninhydrin test. The presence of free thiol groups on any material at any stage of the experiments can be monitored by alkylation with $^{14}$C-iodoacetamide.

Binding can be optimized by examination of % peptides bound versus method of activation (DNA-disulfide or peptide-disulfide), activating agent (2-thiopyridyl or 5-thio-2-nitrobenzoyl), binding mode (batch or column), time of incubation, temperature, and structure of the thiol-containing tether in the DNA.

In another embodiment, equilibrium binding of peptides to thiol-tethered DNA via formation of a disulfide bond can be performed. Peptides can be bound under equilibrium conditions to a thiol-tethered DNA molecule that is bound to a polymer resin, by formation of a disulfide bond between the DNA and the peptides. The disulfide bond between the DNA and peptides can be formed under freely reversible conditions, so the noncovalent interaction of the peptide with DNA will cooperate with the covalent interaction (i.e., disulfide bond formation) to establish a stable complex. These experiments can be carried out in a batch mode.

The thiol-tethered DNA is mixed with a stoichiometric amount of the peptides in a deaerated redox buffer. The redox buffer can be the same as the redox eluent described above. The most important components are the reduced and oxidized forms of a thiol reducing agent, such as 2-thiopyridine, 5-thio-2-nitrobenzoate, dithiothreitol, 2-mercaptoethanol, and N,N'-dimethyl-N,N'-bis (mercaptoacetyl)hydrazine (DMH). The reactants are allowed sufficient time to reach equilibrium. Alternatively, if the DNA is resin-bound, then the resin is pelleted by centrifugation, and the supernatant is removed. The pellet is washed with buffer (lacking added thiols or disulfides) and pelleted again. DNA-bound peptides are then eluted by incubation of the resin under strongly reducing conditions (such as 100 mM dithiothreitol). Ordinarily, parallel incubations (containing different relative amounts of the reduced and oxidized forms of the thiol reducing agent) should be set up and analyzed separately.

The following conditions can be varied to optimize the system: chemical structure of redox eluent, concentration of redox eluent, temperature, flow rate, buffer conditions (pH, ionic strength, addition of organic co-solvents such as trifluoroethanol).

Peptides can be quantified by amino acid analysis and sequenced by automated phenylthiohydantoin methods.

Determination of Binding Molecule-Target Site Binding Affinity

The affinity of a specific binding molecule for the target site on a target can be determined by evaluating the ease with which a reversible bond between the binding molecule and the target can be reversed. These determinations can be made by immobilizing the binding molecule-target complex, such as on a matrix or a resin, and passing a gradient of a reversing agent (an agent which reverses, that is, breaks, or disrupts, the reversible bond and thus releases the binding molecule from the target site) over the immobilized complexes.

In most embodiments of the methods described herein, several species (also referred to herein as a plurality) of test-binding molecules will be screened simultaneously to determine which test-molecule possesses the optimum binding properties. The elution profile allows determination and comparison of the binding affinities of various species of test-binding molecule and selection of the species which represents the optimum or desired structure for the final specific binding molecule.

In the case of a peptide binding molecule complexed to a DNA target molecule by a disulfide bond, the resin bound peptide-DNA complexes are placed, for example, in a chromatography column. A gradient of a reducing agent, e.g., a thiol reagent, is applied to the column. This results in the release of peptides according to their DNA association constants, producing a reductive elution profile. The peptide that elutes last has the highest affinity for the target DNA. This chemical screening process thus provides the optimal residue at the tested position.

Elution of peptides coupled to a target by a disulfide bond can be performed, either in batch or column mode, as follows. Column mode allows more precise control over the elution conditions, since the column can be attached to a commercially available gradient elution system, such as the Fast Protein Liquid Chromatograph (FPLC), Pharmacia) or any similar apparatus. Batch mode operation may be necessary if the conditions required for elution (e.g., high temperatures, long elution times) are incompatible or inconvenient with FPLC.

In the column mode, a redox gradient is passed through the column, causing peptides to be released depending on their redox potential. In the simplest case, the redox gradient consists of mixtures of a thiol or dithiol compound and its corresponding disulfide. In the beginning of the gradient, the redox eluent contains 100% of the disulfide form, and at the end of the gradient, 100% of the thiol (or dithiol) form. Typical redox eluents consist of the thiol and disulfide forms of 2-thiopyridine, 5-thio-2-nitrobenzoate, dithiothreitol, 2-mercaptoethanol, and the N,N'-dimethyl-N,N'-bis (mercaptoacetyl) hydrazine (DMH) reagent recently reported by Whitesides (*J. Org. Chem.* 56:2332–2337 (1991)). The latter may be preferable because of its exceptionally fast kinetics of disulfide reduction.

Elution of peptides from the column is monitored by on-line UV detection at 214 nm and post-column derivation with ninhydrin. Peptides are quantified by amino acid analysis and sequenced by automated phenylthiohydantoin methods. (See FIG. 2).

The following conditions can be varied to optimize elution for speed, ease, or resolution: chemical structure of redox eluent, concentration of redox eluent, slope of gradient, shape of gradient (linear, step, exponential), temperature, flow rate, buffer conditions (pH, ionic strength, addition of organic co-solvents such as trifluoroethanol).

In the batch mode, the resin containing DNA-bound peptides is incubated in an Eppendorf tube with deoxygenated buffer containing the redox eluent. Redox eluents, quantification and identification of peptides are the same as described above for the column mode. The following conditions can be varied to optimize elution: chemical structure of redox eluent, concentration of redox eluent, number and spacing of stepwise elutions, elution time, temperature, buffer conditions (pH, ionic strength, addition of organic co-solvents such as trifluoroethanol).

After the determination of a first optimum modification (i.e., the determination of the optimum residue at a given position of a specific binding molecule) has been made, a second modification can be performed on the test-binding molecule (e.g., the addition of a subsequent residue to a polymeric binding molecule) and the process of evaluating the binding affinity of the newly modified test-binding molecule repeated. This cycle may be repeated a number of times.

As in the first cycle, it will usually be desirable to simultaneously evaluate a number of species (i.e., a plurality) of test-binding molecules (representing a number of different modifications) at each cycle or iteration. For example, in the case of a peptide binding molecule, a plurality of peptide species, differing by the residue at the position (or positions) being optimized, are tested simultaneously. The structure (e.g., in the case of a peptide binding molecule, the particular residue) giving optimum results is selected.

In the case of a peptide binding molecule, a DNA target molecule, and -SH tethers, the following protocol can be used. After the optimum amino acid residue at the second position is determined, a set of tripeptides of the formula $CO_2H$-Cys-XAA-Xaa-$NH_2$ (where XAA is the optimum second position amino acid and Xaa represents any amino acid which lacks an -SH group), is synthesized. Each peptide of the set differs at Xaa. The elution and determination of binding affinity is repeated with the tripeptide to yield the optimum amino acid residue at the third position. The process is repeated until the desired length is reached.

After the iterative methods of synthesis and selection described above have been used to generate the sequence order and structure of a binding molecule, further modifications can be performed on the binding molecule. These modifications may be in the form of a second round of selected optimizations of a different binding molecule characteristic. For example, after an initial determination of the optimum primary sequence of a peptide, a second iterative selection can be applied to determine an optimum level of glycosylation, the effect of cofactors, the effect of homo- or heterodimerization, or the effect of inter- or intra-chain cross linking. These, or other modifications may be tested for their effect on binding by non-iterative methods as well. Additionally, a second iterative selection can be performed to select a second specific binding molecule to form a heterodimer with the binding molecule selected in the first iterative cycle. These two specific binding molecules may be cross-linked by conventional methods.

Modifications such as the formation of homo- or heterodimers, may require alteration of a selected binding molecule. For example, new peptides may be constructed to optimize the spacing of binding units relative to each other and the center of target sites in the DNA, or to allow the introduction of specifically desired residues. Molecular modeling can be used to facilitate the choice of modifications. The sequence specificity of dimerized peptides can be tested by methods known to those skilled in the art (e.g., by competition electrophoretic mobility shift assays, PCR-based target detection assay, or chemical or enzymatic footprinting).

Optimization of Conditions for Determining Binding Affinity

General conditions under which the reversible bond between the binding molecule and the target are formed and broken, and the methods of evaluation of the relationship between reversible bond breakage and binding molecule/target site binding affinity, can be determined by practicing the methods described above with relatively well characterized molecules, as is exemplified in the Example with the GCN4 system.

In addition to the GCN4 system, the X-ray crystal structures of the bacteriophage repressor (Jordan et al., Science 242:893 (1988)) and the murine Zif268 protein (Pavletich et al., Science 252:809 (1991)) bound to their respective DNA sites are deposited in the Brookhaven Protein Data Bank. These can also be retrieved and molecular modeling methods used to trim the structures down to a peptide-bound DNA core structure, as was done with GCN4. Disulfide tethers can be designed to link the resulting peptides to DNA, bearing in mind that the connector should be as short as possible without generating strain. The λ repressor and Zif268 systems are favorable for optimization because they represent respectively, examples of extended and α-helical peptides that bind DNA as isolated units and for which high-resolution structures in the DNA-bound form are available. The α-helices of Zif268, while being part of a zinc finger structural motif, possess all of the residues of that motif that are involved in base-contacts.

DNA-binding peptides designed on the basis of X-ray structures (hereafter referred to as "wild-type" peptides) can be synthesized by standard methodology. Thiol-tethered oligonucleotides designed similarly ("wild-type" oligonucleotides) can be synthesized by methods and linked to a resin, as described above.

The peptides can be tethered to DNA both in solution (for use in high-resolution structural studies) and on a solid matrix (for reductive elution studies). The conditions for forming and releasing the peptide-DNA reversible bond can be optimized using these molecules, as described in the Example. Systems having sequence changes in the DNA or peptide ("mutant" oligonucleotides or peptides) that should disrupt sequence-specific peptide-DNA interactions, can be synthesized in parallel for use as controls or to further investigate elution conditions.

The structures of the DNA-tethered peptide systems constructed in the previous state can be evaluated to discern whether the peptides are associated with DNA in a way that mimics their natural counterparts, or at least in a way that is discernibly sequence-specific. $^1$H-NMR, $^{15}$N-NMR, chemical footprinting, and circular dichroism spectroscopy can be used to evaluate these molecules.

Wild-type and mutant peptide-DNA systems, assembled on a solid matrix in a column can be subjected to reductive elution by a thiol gradient. Parameters affecting elution, such as reducing agent, temperature, pH and slope of the gradient, can be optimized. For example, this approach can be used to find conditions in which wild-type λ and Zif268 peptides are strongly retained (elute late in the gradient) while peptide from mutant systems are not strongly retained (elute early).

Following optimization of the reductive elution conditions for the elongation of wild-type peptides, screening of peptide mixtures can be optimized. The wild-type peptides can be elongated by one peptide unit, using a mixture of any amino acids that lack an -SH group. This 19 peptide mixture can then be coupled to the solid matrix, loaded into a column, and eluted reductively. The late-eluting peptides will be sequenced (e.g., by fast atom bombardment mass spectrometry and/or phenylthiohydantoin degradation). This synthesis and screening process can be repeated iteratively until either the efficiency of synthesis or resolution of the column procedure falls off.

Elongated peptides that are obtained by iterative selection should bind selectively to longer target DNA sequences than the starting peptides. The interaction of these peptides with DNA can be studied by the same methods as described above for the starting peptides.

Moreover, the three dimensional molecule can serve as a guide in choosing the modifications. This can allow the optimization of residues on the same face or side of a structure. For example, in the case of a binding molecule which is a helical molecule, it may be desirable to add subunits in groups of n, where n is the number of subunits involved in one full turn of the helix. In the case of an α-helical protein, wherein n=3.6 residues could be added in groups of 3, with the first two of the three being held constant (e.g., the first two residues being predetermined residues) or in groups of 4 with the first three of the four being held constant (e.g., consisting of predetermined residues) with the final residue, in either case, being varied.

An analogous method can be used to optimize the residues on one face of a β-sheet or β-ribbon structure.

Since residues i, i+2, i+4, i+x, will be on the same surface of a β-ribbon or a β-sheet structure, residues can be added as tripeptide, with the final residue of the peptide being varied.

The desired three-dimensional structure of the binding molecule can also influence choice of modification in other ways. For example, in the case of a peptide, residues which promote the formation of a helical structure, such as 2-aminoisobutyric acid or α-methyl amino acids, can be added. Similarly, pro-gly could be added to a sequence to interrupt a helical structure. A pro-gly series can be added to a peptide sequence to introduce a fold in a β-sheet or β-ribbon structure.

Peptide-on-phage libraries can be used to supply the binding entities in methods of the invention. For example, a fully degenerate phage library could include all peptide test-binding entities to be tested in one batch.

The peptides could be coupled to the target and eluted as a batch.

Figure 3:
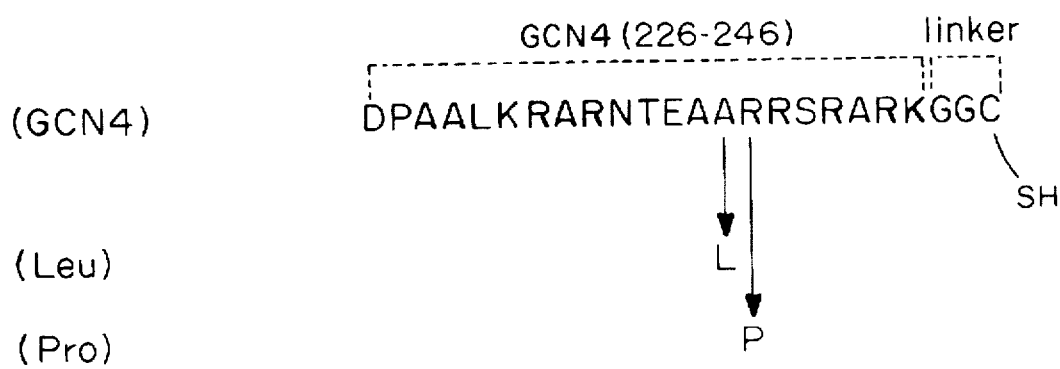
FIG. 3 shows the components of the GCN4 binding system, including the oligonucleotides designated WT, a 39 bp oligonucleotide with a modified adenine residue incorporated into the DNA adjacent to the 5 bp GCN4 recognition half-site (shaded in gray) (SEQ ID NO: 1); control oligonucleotide M2 (SEQ ID NO: 2); control oligonucleotide M3 (SEQ ID NO: 3) the G-CN4 basic region with a 3-residue linker (SEQ ID NO: 4); a mutant peptide with leucine replacing alanine 239 (SEQ ID NO: 5) and a mutant peptide with proline replacing arginine 240 (SEQ ID NO: 6).

Demonstration of the Binding Specificity of GCN4 and Mutant GCN4 Peptides to DNA The GCN4 system features a reversible covalent bond between the peptide and DNA such that the formation of the sequence-specific complex incurs no loss of translational entropy. It utilizes a modified synthetic oligonucleotide having a tethered thiol group in major groove (FIG. 3). A peptide is then attached to the DNA via a disulfide bond between the thiol group of the tether and a terminal cysteine residue in the peptide. Once the linkage is formed, two possible states could be envisioned: one in which the peptide is essentially free in solution (uncomplexed), and one in which the peptide is associated sequence-specifically with DNA. In this system, formation of the specific complex from the uncomplexed state is associated with no change in translational entropy, since the two binding partners are physically linked. In other words, physical linkage of the peptide to DNA efficiently increases the local concentration of the two binding partners and therefore increases their likelihood of association. This permits the testing of sequence-specific interactions of very short peptides.

Disulfide bonds have the unusual property of being covalent yet readily broken down under mild conditions. This provides a means by which to assay the strength of the peptide-DNA interaction, and to screen peptide mixtures for tight-binding peptides. For example, consider the attack of an exogenous thiol reagent (RSH) on the disulfide bond of a peptide-DNA complex. If the linked peptide is in the uncomplexed state, it will freely diffuse into solution; reversal of this reaction is bimolecular and therefore disfavored at low peptide concentrations. On the other hand, when the peptide is associated with DNA, cleavage of the disulfide bond is readily reversible, since its reformation is an intramolecular reaction. Considering these two limiting cases and gradations in between, the strength of the disulfide bond in a disulfide-linked peptide-DNA complex is directly related to the strength of the non-covalent peptide-DNA association (Kd).

The experimental design described in the Example, is based on a DNA-protein complex derived from the yeast transcriptional activator GCN4. A 39 bp oligonucleotide SEQ ID NO.:1 with a modified adenine residue incorporated into the DNA adjacent to the 5 bp GCN4 recognition half-site (shaded in gray) was synthesized using conventional methods (FIG. 3). This adenine bears a protected thioethyl or thiopropyl group protruding into the DNA major groove, serving as a specific locus for the attachment of the cysteine bearing peptide. The sequence of the peptide and the site for thiol incorporation were chosen in order to minimize the length of the linker between the peptide and DNA. Two control oligonucleotides having the same structure except for a single base pair mutation in the GCN4 binding half-site were also synthesized (See FIG. 3, M2 SEQ ID NO.:2 and M3SEQ ID NO.:3).

The synthetic peptide contains 21 residues derived from GCN4 basic region and a 3-residue linker SEQ ID NO.:4. Two additional "mutant" peptides were made, each having a single amino acid change (Leu SEQ ID NO.:5 and Pro SEQ ID NO.:6, FIG. 3). The leucine mutation replaces an alanine 239 residue that contacts the methyl group of thymine at the fourth position and it has been shown previously to prevent binding of dimerized GCN4 protein. The proline mutation is designed to destabilize the α-helix by replacing the arginine 240 that contacts the phosphate backbone of DNA.

Various combinations of double-stranded oligonucleotides (end-labeled with $^{32}P$) and peptides were coupled by a disulfide bond as described in the Example. Such covalent complexes were incubated in the presence of DNAse I at different temperatures and resulting fragments were resolved on 20% denaturing gel. (Galas, D. J. and Schmitz, A., Nucleic Acid Res. 5:3157–3170 (1978)). The DNAse protection patterns imply that tethered peptides interact with DNA in a sequence-specific manner. For example, if an oligo contains the wild-type GCN4 binding half-site, the tethered GCN4 peptide protects this region from digestion by DNAse; the same peptide does not protect DNA containing mutation M3. The presence of mutation M2 causes partial DNAse protection. It has been shown that the alanine 239 to leucine substitution prevents the binding of a mutant protein. Both the wild-type and Leu peptide protect wt DNA at 0° C. However, if the same assay is performed at 5° C., 10° C. or 20° C., the Leu complex shows weaker protection relative to the wild-type peptide. The Pro mutant does not significantly protect DNA at any temperature.

Figure 4:
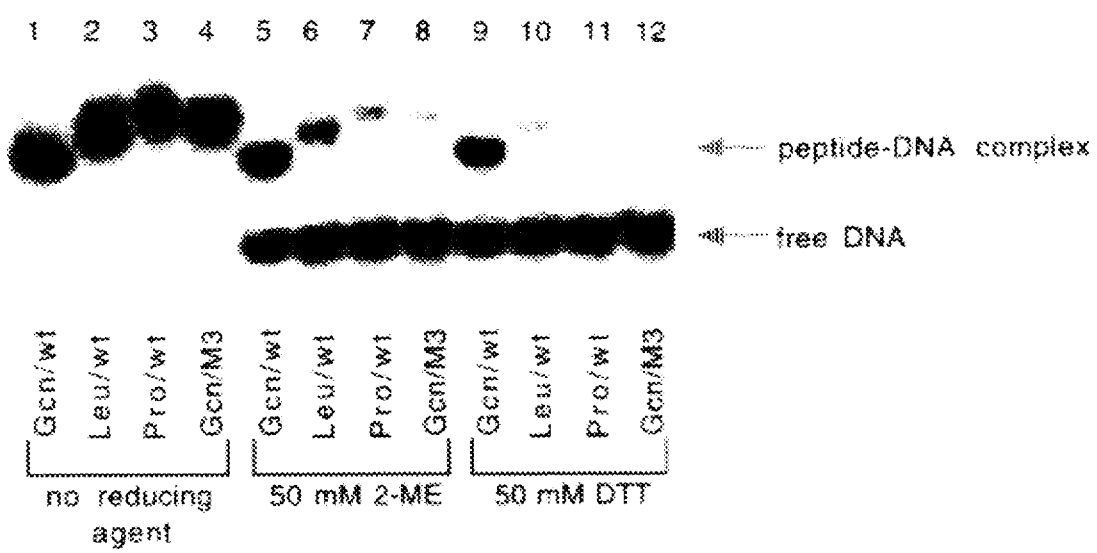
FIG. 4 shows the results of an experiment designed to test if the reduction potential of the disulfide bond corresponds to the affinity of the peptide for the adjacent DNA sequence. Peptide-DNA complexes were resolved by 20% non-denaturing PAGE.

To test if the reduction potential of the disulfide bond corresponds to the affinity of the peptide for the adjacent DNA sequence, wild-type and mutant double-stranded DNA-peptide complexes were incubated in the presence of reducing agents 2-mercaptoethanol (2-ME) or dithiothreitol (DTT). (FIG. 4) The free (lower bands) vs. coupled DNA molecules (upper bands) were resolved on 20% nondenaturing polyacrylamide gel after. The wild-type peptide-DNA complex (wt) was consistently more resistant to reduction than the complex having mutation in either peptide (L, P) or DNA sequence (M3). Peptide-DNA complexes differ with respect to the gel mobility as well. The mutant complexes (L, P, M3) have lower gel mobility than the wild-type complex (wt), although the corresponding free (uncomplexed) DNA molecules run at the same speed.

The invention will now be illustrated further and more specifically by the following Exemplification.

EXAMPLE

Disulfide-linked-peptide-DNA Complexes

1. Synthesis and purification of peptides

All GCN4-derived peptides were synthesized on Applied Biosystems Model 431A peptide synthesizer with standard reaction cycles. Peptides were deprotected and cleaved from the resin by incubation in the mixture of trifluoroacetic acid:phenol:anisole:ethanedithiol (94:2:2:2) for 4 hours at room temperature. The peptide solution was precipitated and washed 4–5 times with ice-cold diethyl ether. The pellet was dried with air, dissolved in 1 ml of 10% acetic acid and lyophilized. The peptide was purified by HPLC with ZORBAX reverse-phase C-8 semi-preparative column (DuPont Instruments) and a linear gradient of acetonitrile-water with 0.1% TFA. Fast atom bombardment mass spectroscopy revealed a peak at 2613.07 which agrees with the calculated mass of 2611.97. Collected fractions were lyophilized and stored at −20° C.

2. Synthesis and purification of DNA oligonucleotides

All oligonucleotides were synthesized on an Applied Biosystems DNA synthesizer Model 381A using conventional and modified phosphoramidites according to the "convertible nucleoside approach" described in MacMillan, A. M. and Verdine, G. L., J. Org. Chem. 55:5931 (1990) and Ferentz, A. E., and Verdine, G. L., J. Am. Chem. Soc. 113:4000–4002 (1991). The displacement reaction was done with the disulfide of aminepropanethiol to yield modified oligonucleotides with $N^6$-thioalkyl-dA or $N^4$-thioalkyl-dC, protected as mixed disulfides. Both modified and unmodified oligonucleotides were purified by polyacrylamide gel electrophoresis (PAGE) on 20% denaturing gels.

Annealing of different modified oligonucleotides with the corresponding complementary strands produced four double-stranded probes carrying the tethered disulfide at four different positions with respect to the GCN4-binding half-site.

3. Reduction of peptides

The lyophilized GCN4-derived peptide was dissolved in 0.1 ml of 1xTE8 (Tris-EDTA buffer, pH 8) and peptide concentration determined by UV spectroscopy (210 and 220 nm) was 3 mM. The peptide was reduced by the addition of 1 microliter of 1:10 dilution of 2-mercaptoethanol stock (14.4M, obtained from Bio-Rad Laboratories) and incubated at 500 for 30 minutes. The reaction mixture was subsequently lyophilized in the speedvac concentrator (Savant) to evaporate 2-mercaptoethanol and the dry pellet was dissolved in 0.1 ml of 10xTE8.

4. Coupling of the peptide to DNA

About 20 nmols of an HPLC purified peptide (dissolved in water) was incubated in the presence of 100 mM 2-mercaproethanol at 40° C. for 30 min. The reaction mixture was then liophilized in the speedvac for 1 hours. Dried reduced peptide was redissolved in water (in 10 microliters) and mixed with 2–3 nmols of single-stranded thiol containing oligo. The coupling reaction was performed in 5 mM KCl and 20 mM Tris pH 7.5 for about 8–16 hours at room temperature.

5. Purification of the single-stranded oligo-peptide

Purification was performed on Millipore Gen-Pak Fax anion-exchange HPLC column in the TE/TE+M NaCl buffer system in the presence of 10% acetonitrile at pH 8. The TE+NaCl (buffer B) gradient started from 20% and rose to 60% in 40 minutes. The peak corresponding to the DNA-peptide complex was collected in about 300–500 microliters. The concentration was determined by UV spectroscopy.

6. DNAse Protection Experiments

About 1 picomole of purified complex was mixed with 0.2 picomoles of $^{32}P$ end-labeled complementary oligonucleotide in 50 microliters of 4–200mM binding buffer. The annealing was done at room temperature for 20 minutes and reaction was subsequently transferred to a desired temperature (0°–20° C. in water bath) for another 15 minutes. The digestion by DNAse was done in a conventional way. Reactions were extracted with phenol and chloroform, precipitated and resolved on 20% denaturing gel.

7. Reduction Gel-shift Experiments

Annealing of the oligonucleotide-peptide complex with the complementary oligonucleotide was done as described above, in the binding buffer of the same composition and desired pH (7.5 or 8.5). 2-ME or DTT was added and reactions were incubated at defined temperature in a water bath. Glycerol-running dye mixture was added (final concentration of glycerol is 5%) and reactions were loaded on 20% nondenaturing gel and run at low voltage (up to 120 V) for 16–24 hours at room temperature. (See FIG. 4).

Equivalents

Those skilled in the art will recognize, or be able to ascertain using no more than routine experimentation, many equivalents to the specific embodiments of the invention described herein. Such equivalents are intended to be encompassed by the following claims.

The invention claimed is:

1. A method of identifying a sequence-specific DNA binding molecule, comprising the steps of:
   a) combining: 1) a target DNA sequence comprising a first thiol group which forms a disulfide bond with a second thiol group and; 2) a test-molecule which is an organic molecule to be assessed for its ability to bind a region of the target DNA sequence, said test-molecule comprising the second thiol group, thereby producing a combination;
   b) maintaining the combination produced in a) under conditions appropriate for formation of a disulfide bond between the first thiol group of the target DNA and the second thiol group of the test molecule, and binding of the test-molecule to the target DNA sequence, thereby producing target DNA sequence-test-molecule complexes;
   c) subjecting complexes produced in b) to a reducing agent which cleaves the disulfide bond, thereby producing a mixture which contains complexes, uncomplexed target DNA sequences, and uncomplexed test-molecules; and
   d) determining the identity of test-molecules present in the complexes, wherein the presence of a test-molecule in a complex is an indication of a sequence-specific DNA binding molecule.

2. The method of claim 1 wherein the test molecule of step a) comprises a peptide or nucleic acid.

3. The method of claim 1 further comprising attaching the DNA molecule to an immobilizing matrix, and wherein subjecting complexes to the reducing agent comprises contacting the complex with a concentration gradient of the reducing agent, and determining the ability of the reducing agent to cleave the disulfide bond comprises determining the ability at the reducing agent to elute the test-molecule from the immobilized DNA.

4. The method of claim 3, wherein the test-molecule comprises a peptide comprising a first and second subunit, the first subunit comprises a first amino acid residue comprising an -SH group and the second subunit comprises a second amino acid residue which does not contain an -SH group.

5. The method of claim 4, wherein the first subunit comprises cysteine.

6. The method of claim 1, wherein
   step a) further comprises providing a plurality of test-molecules, each of the test molecules comprising a thiol group,
   step b) further comprises maintaining a plurality of the test-molecules with a plurality of the DNA molecules to form a plurality of complexes, each of the complexes comprising a test-molecule linked by a disulfide bond to a DNA molecule, step c) further comprises subjecting a plurality of the complexes to a reducing agent to cleave the disulfide bonds; and step d) further comprises determining the susceptibility of the bonds to the reducing agent wherein the susceptibility of the bonds is an inverse measure of the ability of a test molecule to bind to the DNA molecule.

7. The method of claim 1 wherein in step d), test-molecules present in the complexes are identified by a method selected from the group consisting of: $^1$H-NMR spectroscopy, $^{15}$H-NMR spectroscopy, chemical footprinting assay, circular dichroism spectroscopy and electrophoretic mobility shift assay.

8. A method of evaluating the affinity of a specific binding molecule for a target DNA sequence, wherein the specific binding molecule is an organic molecule tethered to the target DNA sequence via a disulfide bond, and the affinity of the specific binding molecule is directly related to the susceptibility of the bond to cleavage under reducing conditions, comprising the steps of:

a) combining a desired target DNA sequence comprising a first thiol group which forms a disulfide bond with a second thiol group, and a test-molecule comprising the second thiol group, thereby producing a combination;

b) maintaining the combination produced in a) under conditions appropriate for formation of a disulfide bond between the first thiol group and the second thiol group, and binding of the test-molecule to the target DNA sequence, thereby producing target-test-molecule complexes;

c) subjecting complexes produced in b) to a reducing agent at a concentration sufficient to result in cleavage of the disulfide bond;

d) determining whether the bond tethering the specific binding molecule to the target DNA sequence is cleaved under the conditions of c); and e) repeating steps c) and d) with increasing concentrations of reducing agent until the bond tethering the specific binding molecule to the target DNA sequence is cleaved, wherein the concentration of cleavage agent required to cause reversal of the bond is an indication of the susceptibility of the bond to cleavage, and susceptibility of the bond to cleavage is an indication of the affinity of the specific binding molecule for the target DNA sequence.

9. The method of claim 8 wherein the specific binding molecule comprises a peptide or nucleic acid.

10. A method of evaluating the affinity of a specific binding molecule for a target DNA sequence, wherein the specific binding molecule is an organic molecule tethered to the target DNA sequence via a disulfide bond, and the affinity of the specific binding molecule is directly related to the susceptibility of the bond to cleavage under reducing conditions, comprising the steps of:

a) combining a target DNA sequence comprising a first thiol group which forms a disulfide bond with a second thiol group, and a test-molecule comprising the second thiol group, thereby producing a combination;

b) maintaining the combination produced in a) under conditions appropriate for formation of a disulfide bond between the first thiol group of the target DNA and the second thiol group of the test molecule, and binding of the test-molecule to the target DNA sequence, thereby producing desired target-test-molecule complexes;

c) subjecting complexes produced in b) to a reducing agent at a concentration sufficient to result in cleavage of the disulfide bond for a length of time;

d) determining whether the bond tethering the specific binding molecule to the target DNA sequence is cleaved under the conditions of c); and e) repeating steps c) and d) for increasingly longer lengths of time until the bond tethering the specific binding molecule to the target DNA sequence is cleaved, wherein the length of time required to cause cleavage of the bond is an indication of the susceptibility of the bond to cleavage, and susceptibility of the bond to cleavage is an indication of the affinity of the specific binding molecule for the target DNA sequence.

11. The method of claim 10 wherein the specific binding molecule comprises a peptide or nucleic acid.

12. The method of claim 11 wherein the peptide is a monomer.

13. A method of identifying a monomeric sequence-specific DNA binding peptide comprising the steps of:

a) combining a target DNA sequence with a tether having a thiol group and a monomeric peptide with a tether having a thiol group, thereby producing a combination;

b) maintaining the combination produced in a) under conditions appropriate for formation of a disulfide bond between the thiol group on the target DNA sequence and the thiol group on the monomeric peptide, and binding of the peptide to the target DNA sequence, thereby producing target DNA sequence-peptide complexes;

c) subjecting complexes produced in b) to a reducing agent resulting in reduction of the disulfide bond, wherein if the peptide is bound to the target DNA sequence with sequence-specificity, the disulfide bond reforms and the target DNA sequence-peptide complex remains intact; and d) determining the presence of target DNA sequence-peptide complexes, wherein the presence of a target DNA sequence-peptide complex is an indication of a monomeric peptide that binds to the target DNA with sequence-specificity.

14. A method of simultaneously screening a mixture comprising a plurality of peptides of different amino acid sequences to identify a sequence-specific DNA binding peptide, comprising the steps of:

a) combining: 1) a target DNA sequence comprising a first thiol group which forms a disulfide bond with a second thiol group and;

2) a mixture of test-peptides comprising amino acid sequences to be assessed for their ability to bind to the target DNA, said test-peptides comprising the second thiol group, thereby producing a combination;

b) maintaining the combination produced in a) under conditions appropriate for formation of a disulfide bond between the first thiol group of the target DNA and the second thiol group of the test molecule, and binding of the test-peptides to the target DNA sequence, thereby producing target DNA sequence-test-peptide complexes;

c) subjecting complexes produced in b) to a reducing agent which cleaves d) determining the identity of test-peptides present in complexes, wherein the presence of a test-peptide in a complex is an indication of a sequence-specific DNA binding peptide.

* * * * *

UNITED STATES PATENT AND TRADEMARK OFFICE
CERTIFICATE OF CORRECTION

PATENT NO. :  5,783,384
DATED      :  July 21, 1998
INVENTOR(S) : Gregory L. Verdine It is certified that error appears in the above-identified patent and that said Letters Patent is hereby corrected as shown below:

In Claim 3, line 51, replace "at" with ---of---.

Signed and Sealed this

Sixteenth Day of March, 1999

Attest:

Q. TODD DICKINSON

*Attesting Officer*     *Acting Commissioner of Patents and Trademarks*